US009610051B2

(12) United States Patent
Beekman (10) Patent No.: US 9,610,051 B2
(45) Date of Patent: Apr. 4, 2017

(54) SCANNING OF A HUMAN BODY PART WITH HIGH-ENERGY RADIATION EMITTED BY THE BODY PART

(71) Applicant: Milabs B.V., Utrecht (NL)

(72) Inventor: Frederik Johannes Beekman, Utrecht (NL)

(73) Assignee: MILABS B.V., Utrecht (NL)

( * ) Notice: Subject to any disclaimer, the term of this patent is extended or adjusted under 35 U.S.C. 154(b) by 0 days.

(21) Appl. No.: 15/301,136

(22) PCT Filed: Apr. 2, 2015

(86) PCT No.: PCT/NL2015/050212
§ 371 (c)(1),
(2) Date: Sep. 30, 2016

(87) PCT Pub. No.: WO2015/152720
PCT Pub. Date: Oct. 8, 2015

(65) Prior Publication Data
US 2017/0020467 A1    Jan. 26, 2017

(30) Foreign Application Priority Data
Apr. 2, 2014 (NL) ..................................... 2012546

(51) Int. Cl.
*G01T 1/166* (2006.01)
*A61B 6/06* (2006.01)
(Continued)

(52) U.S. Cl.
CPC .............. *A61B 6/06* (2013.01); *A61B 6/0414* (2013.01); *A61B 6/4258* (2013.01); *A61B 6/502* (2013.01); *G01T 1/1648* (2013.01)

(58) Field of Classification Search
CPC ....... A61B 6/037; A61B 6/502; A61B 6/0414; A61B 6/4258
See application file for complete search history.

(56) References Cited

U.S. PATENT DOCUMENTS

| 5,462,056 A | 10/1995 | Hawman et al. |
| 2009/0022279 A1 | 1/2009 | Wieczorek |

(Continued)

FOREIGN PATENT DOCUMENTS

| EP | 0526970 A2 | 2/1993 |
| EP | 2073039 A1 | 6/2009 |

(Continued)

*Primary Examiner* — Mark R Gaworecki
*Assistant Examiner* — Kenneth J Malkowski
(74) *Attorney, Agent, or Firm* — Hoffmann & Baron, LLP (57) ABSTRACT

A scanner for scanning a body part of a human, such as, for example, a breast of a woman includes a supporting part for the upper body of a human, a receiving space for the body part to be scanned, possibly a compression device for pressing against the body part introduced into the receiving space, and a camera which is arranged to form an image of the body part introduced into the receiving space and pressed against by the compression device, with the aid of high-energy radiation emitted by the body part. The camera includes a collimator having a movable collimator part which has an incident surface facing towards the receiving space. The collimator defines and delimits an astigmatic, two-dimensional collection of radiation channels for the high-energy radiation.

16 Claims, 4 Drawing Sheets

(51) Int. Cl.
*A61B 6/00* (2006.01)
*A61B 6/04* (2006.01)
*G01T 1/164* (2006.01)

(56) References Cited

U.S. PATENT DOCUMENTS

| | | |
|---|---|---|
| 2010/0260316 A1 | 10/2010 | Stein et al. |
| 2010/0329419 A1 | 12/2010 | Blevis |
| 2013/0158389 A1 | 6/2013 | O'Connor |
| 2014/0093035 A1 | 4/2014 | Beekman |

FOREIGN PATENT DOCUMENTS

| | | |
|---|---|---|
| EP | 2491864 A1 | 8/2012 |
| WO | 2010/014001 A2 | 2/2010 |
| WO | 2011/096584 A1 | 8/2011 |

SCANNING OF A HUMAN BODY PART WITH HIGH-ENERGY RADIATION EMITTED BY THE BODY PART

CROSS-REFERENCE TO RELATED APPLICATIONS

This application is the National Stage of International Application No. PCT/NL2015/050212 filed Apr. 2, 2015, which claims the benefit of Netherlands Application No. NL 2012546, filed Apr. 2, 2014, the contents of which is incorporated by reference herein.

FIELD OF THE INVENTION

The present invention relates to the scanning of a body part of a human, such as, for example, a breast of a woman, with the aid of high-energy radiation emitted by the body part, for example gamma radiation.

BACKGROUND OF THE INVENTION

Document WO2010/014001 describes a breast scanner having a positioning device, which latter comprises a frame supporting at least two positioning components—embodied as positioning plates—which define between them a receiving space for a breast of a person, which breast is to be scanned. The breast to be scanned can be introduced into this receiving space in an intended direction of introduction. At least one of the positioning components is placed movably on the frame in a first direction substantially towards another positioning plate of the at least two positioning components. The positioning components are arranged to touch, for example to compress the breast if placed between the positioning components. The known scanner further comprises a gamma camera, which is arranged to portray a volume in the receiving space on the basis of high-energy radiation, especially gamma radiation, emitted by the breast.

The gamma camera of the said known scanner comprises a plate-like collimator part, which is provided with at least a first multitude of focused pinholes, each having an individual field of view, i.e. part of the object which is imaged through the pinhole, wherein the individual fields of view of the first multitude of pinholes define a common central field of view as that part of the space which is seen through each of the first multitude of pinholes. The gamma camera further comprises a gamma-sensitive detector, which is arranged to receive images from the collimator. The plate-like collimator part is movable in a plane which is substantially parallel to one of the positioning components and is movable in that plane, preferably in mutually perpendicular directions in that plane. The scanner further comprises a collimator moving device, which is arranged to move the plate-like collimator part in that plane in a controlled manner.

This scanner, known from WO2010/014001, has the drawback of an unfavourable relationship between, on the one hand, a relatively large detector surface, necessary to make a scan of the desired volume, and, on the other hand, good sensitivity and resolution, especially if a part of the breast is scanned. This results in an uneconomical use of the difficult to produce and expensive detector material, which is a factor in preventing the use of such scanners on a larger scale.

OBJECT OF THE INVENTION

An object of the present invention is to provide a scanner which at least partially counters this drawback, or at least constitutes a useful alternative for existing scanners. In addition, an object is to enable more efficient use of the detector surface, and thus make cost savings possible. It is also an object both to keep the sensitivity high, since that allows a lower radiation load for the person to be examined, and to have a high resolution, since that allows a better image and thus better diagnosis.

SUMMARY OF THE INVENTION

The invention achieves one or more of the above-stated objects with a scanner of which the collimator comprises a movable collimator part, which has an incident surface facing towards the receiving space, wherein the camera comprises an associated collimator moving device which is adapted to move the movable collimator part in a direction of movement substantially parallel to the incident surface.

The collimator defines and delimits an astigmatic, two-dimensional collection of radiation channels for high-energy radiation emitted by the body part, for example the breast of a woman. The radiation channels point towards a first line extending at a first distance d1 from the incident surface, which first line is substantially parallel to the longitudinal axis of the receiving space for the body part to be scanned. The radiation channels also point towards a second line, which extends on the opposite side of the receiving space relative to the collimator, at a second distance d2 from the incident surface which is greater than the first distance d1. The second line extends transversely to the first line and parallel to the said incident surface.

The notion behind the scanner is that, by providing the camera of the scanner with an astigmatic collimator, better use can be made of the geometry of the majority of body parts to be scanned. After all, with such scanners these are often somewhat elongated body parts protruding from the body, and the body part which is to be scanned is always attached to another part of the body. For the sake of the quality of the scan and/or because of the complexity of the associated image processing, it is desirable to prevent direct radiation via the collimator holes (radiation channels) from that other body part. A screening of that other body part by a wall or table with lead or the like is only partially effective in a scanner. For instance, a female breast is attached to the chest and the rest of the upper body. In order to obtain a scan of the breast, it is desirable not to jointly scan the chest et cetera, since the heart and the liver, for example, can absorb much radioactivity, which can cause artefacts in the image of the breast. By accepting in the scanner according to the invention a small convergence of the radiation channels in the one direction, the region which is actually scanned can be kept relatively narrow, and thus can be well directed with respect to the body part to be scanned, especially a female breast, wherein unwanted detection of radiation from other body parts, such as the chest, can be effectively prevented. By on the other hand, that is to say in the other direction, setting a large convergence or focusing, the "fields of view" of the radiation channels in this direction will overlap each other fairly close together relatively strongly, so that a high sensitivity and a high resolution is achieved. Hence, even though the volume scanned in a specific scanning position of the movable collimator part also becomes small, this is then resolved again by displacing at least a movable part of the collimator, so that a multiplicity of scanning positions is realized and so that the whole desired volume can still be scanned.

By high-energy radiation is here meant radiation which is used in radiological examination based on radioactive markers, thus with radioactive decay. In practical embodiments, this will relate especially to gamma radiation, such as, for example, emanating from technetium or the like.

The high-energy radiation, especially gamma radiation, emanates in practical applications from a radioactive marker which has been taken in by the person, for example injected, inhaled, or swallowed by the person. For example, a radioactive pharmaceutical preparation, which is absorbed by different tissues in different measure, is used. The one or more cameras observe the radiation which is then emitted.

The "first line extending at a first distance from the said incident surface" lies in the receiving space, or possibly even, with respect to that collimator surface, on the opposite side of the receiving space. These are thus convergent radiation channels.

The said incident surface of the collimator is preferably flat, but in a possible embodiment that surface can be curved. In the case of a curved incident surface, by "parallel to the surface of the collimator" is meant that the second line is at least locally parallel to that surface.

In a practical advantageous embodiment, the said incident surface is entirely flat, preferably likewise an adjacent side of a possible compression component.

By "substantially parallel to" a longitudinal axis of the receiving space/the first line/the second line/et cetera" is meant within 10 degrees with respect to this longitudinal axis/first line/second line/et cetera.

Possible embodiments of the scanner are described in the dependent claims, a well as in the following description.

Below, reference is made to the breast (mamma) of a woman, but instead of a breast the scanner according to the invention is also conceivable for other body parts, such as, especially, an arm, (part of) a shoulder, armpit or the like. The receiving space can also be such that two female breasts can be accommodated in the space at the same time.

In some embodiments the collimator is asymmetrical, in particular with respect to a plane perpendicular to the longitudinal axis of the receiving space, i.e. in the use of an illustrative embodiment of the scanner, vertically asymmetrical. Notably, more radiation channels point towards the supporting part than away from it. Here too, use is made of the geometry of the body part to be scanned, which body part, often on one side, is attached to the trunk. There is then little use in having on the trunk side also radiation channels which would themselves point away from the supporting part (in a practical embodiment "downwards").

In some embodiments, the scanner further comprises an actuator for pressing against a movable compression component. Such an actuator then provides for the pressing together, compression, of, for example, the breast, so that this flattens and the tissue can be more easily and more accurately scanned. The actuator can be, for example, a pneumatic actuator, such as having a manually operated sphygmomanometer balloon pump, which the person to be examined may possibly operate herself in order to keep the pressure comfortable. It can also be an automated actuator, for example having a computer control system and a compression application program loaded therein. The actuator can also be realized differently, for example with a spindle drive or some other purely mechanical actuator. In addition, it is possible for no actuator to be provided, but for the compression to be applied entirely manually. The pressing direction of the compression component is preferably perpendicular to the compression component, in particular if the compression component is a compression plate, and advantageously is also perpendicular to that surface of the collimator which is facing towards the compression component, in particular perpendicular to a plate-like collimator part. In the pressing operation, a smallest possible shearing stress or friction shall be developed on the breast, which is not only more comfortable, but also causes less deformation, such as wrinkling, of the breast and hence less misinterpretation of images.

Note that the one or more compression components is/are advantageously of flat design, at least on the side of the collimator and, for example, also on the side of the receiving space, for example is/are realized as a compression plate having parallel faces. The flat design on the side of the collimator enables a shortest possible distance to the moving collimator part. For example, only a small clearance is present between the compression component and the collimator in order to prevent mutual friction, especially with a view to a scanning movement of the movable collimator part with respect to a compression component held stationary during the scanning process and the body part compressed by the compression component.

For example, the supply of a gas under pressure, for example air, between the movable collimator part and the compression plate is provided, in order to reduce or eliminate friction, in the form of a gas bearing. For example, a heating device is provided to heat the gas, so that the temperature of the compression plate can be thereby controlled. It will be clear that this measure can be applied regardless of the design of the collimator.

The direction of movement of at least the movable part of the collimator is preferably parallel to the second line, preferably substantially parallel to the compression component, and preferably also parallel to the supporting part, so that the collimator remains not only as close as possible to the compression component and thus to the breast to be scanned, but also at one and the same distance from the upper body.

Preferably, the movement in this direction of movement is a rectilinear movement, wherein possibly, in the case of movement in one direction, a plurality of projections are collected at different scanning positions of the movable collimator part with respect to the body part to be scanned, the other movement being merely a return movement. In the case of movement in each of these directions, a plurality of images can also be collected, of course, with the aid of the gamma camera.

However, it is alternatively or additionally possible to provide a second direction of movement of the movable collimator part, different from the first direction of movement, for example at right angles to the first direction of movement. For example, the second direction of movement is parallel to both the compression component and the longitudinal axis of the receiving space, or else a combination with the first direction of movement. In a suitable embodiment of the two-dimensional collection of radiation channels of the astigmatic collimator with respect to the dimensions of the body part to be scanned, possibly taking account of compression thereof by a possible compression device, a movement parallel to the longitudinal axis is in principle, however, not necessary, and preferably absent.

In an embodiment in which the second line is displaced towards infinity, whereby the radiation channels run in one direction (virtually) in parallel, for example substantially parallel to the support surface of a supporting table, it is practical if the direction of movement of the movable collimator part for the execution of the scanning process is directed parallel to the surface of the movable collimator part and parallel to the support surface of the supporting member.

In a practical embodiment, the scanner has a table, on which the person comes to lie with at least the upper body, and the one or more cameras are arranged beneath the table, wherein the movable collimator part is a collimator plate which stands vertically beside a receiving space for the body part, which receiving space is accessible from above via an introduction opening in the table. Preferably, the movable collimator plate is a flat plate which is movable in a straight line back and forth in its plane, preferably in a horizontal direction, wherein the top margin of the collimator plate adjoins, preferably with small clearance, the bottom side of the table. Preferably, a plate which is permeable to the radiation is then present between the movable collimator plate and the body part, which plate, for example a plastics plate, such as, for example, a compression plate as described herein, is held stationary during the scanning process.

In some embodiments, the first line lies at a distance, also termed the first distance, between 2 and 25 cm from the said incident surface of the collimator. For example, the first line lies at a distance between 4 and 12 cm, for example at approximately 4 cm. A high sensitivity can thus be achieved owing to the small distance between the collimator (in fact the detector) and the first line, in which the individual fields of view of the radiation channels meet. Also a lot of angle information can be gathered by virtue of the short distance to the collimator, and thus a high accuracy. In this context, a short distance can provide a better tumour detection but is harder to make, whilst a greater distance gives, for example, an excellent screening efficiency. In a particular embodiment, the first line substantially coincides with the longitudinal axis of the receiving space. The sensitivity, averaged over the breast, is thus attractive. Nonetheless, other positions of the first line are possible.

It is possible to provide a scanner having different, exchangeable collimators or collimator parts, for example each with a different first distance to the first line. The collimator, and hence the scanner, can thus be optimally adapted to different body parts, such as different female breast formats.

The invention also relates to a system of a scanner as described herein, comprising a collimator which defines and delimits an astigmatic, two-dimensional collection of radiation channels for the high-energy radiation emitted by the body part to be scanned, wherein at least one camera thereof is arranged for the exchange of the movable collimator part, for example a movable collimator plate, and wherein the system further comprises a set of several exchangeable movable collimator parts, each having a different first distance to the first line and/or to the second line.

In some embodiments, the second line lies substantially parallel to the direction of movement of the movable collimator part, so that a constant sensitivity during the movement in this direction, that is to say during the scanning, can be achieved. In particular, the second line, and thus preferably the direction of movement, stands perpendicular to the longitudinal axis of the receiving space, so that the breast can be efficiently scanned. Advantageously, the longitudinal axis of the receiving space, the pressing direction, and the direction of movement along the supporting part stand mutually parallel to one another, so that not only can the scanning proceed efficiently, but also the image reconstruction becomes relatively simple. Nonetheless, other positions, such as at an angle, are certainly possible.

In some embodiments, the second line lies at a distance, also termed the second distance, between 20 and 50 cm from the said incident collimator surface. Thus, in view of the dimensions of the majority of female breasts, certainly in combination with a compression thereof, the scanner is able to scan at least a large part of the breast or other body part, that is to say without cutting off a part thereof, and above all without a very large required detector surface.

In some embodiments, the second line extends substantially level with the supporting part. In one embodiment, this signifies that the uppermost radiation channels, thus situated, during use, closest to the supporting part, shall "look" virtually parallel to the supporting part, and the lower situated radiation channels, only once they are relatively far away, shall look to above the supporting part. In combination with the relatively large distance away at which the second line is situated, this has the advantage, inter alia, that the last-named radiation channels, and thus, in fact, also all radiation channels together, can be effectively be screened from radiation from the rest of the body, whilst tumours and the like which however still lie deep in the breast can be seen by the scanner. After all, the supporting component can very well be provided around the introduction opening with radiation screening material, such as a lead plate. In an embodiment according to the prior art, where the radiation channels meet in the receiving space in order to increase the sensitivity, the lowermost radiation channels, which look most upwards, can consequently also still receive radiation from, for example, the chest cavity, comprising the heart and other organs.

It is noted that the supporting part does not in principle need to be entirely flat. In view of the human anatomy, the supporting part may preferably have substantially at the least a flattened shape, for example within a distance of 20-100 cm to the longitudinal axis, for example in an annular region around the introduction opening. Possibly, a region of the supporting part which lies further from the introduction opening is situated high up, for example in an annular region situated around a bearing. The second line is possibly located level with the higher situated region of the supporting part, in which case the second line is placed also high up, for example as high or higher than a plane through and parallel to the introduction opening.

By "substantially level with the supporting part" is here meant within a predetermined distance to the actual supporting part, wherein this predetermined distance preferably amounts to no more than 10 cm, and wherein the second line lies preferably in or below the supporting part, at no more than 5 cm distance from the supporting part. In actuality, the scanner can look deepest into the breast if the second line is situated as high as possible, without, however, lying (clearly) above the supporting part.

In some embodiments, the ratio between the first distance and the second distance lies between 1:2 and 1:10. With such ratios, a good compromise turns out to be possible between high sensitivity, limited detector surface and flexibility in being able to scan the body part sufficiently fully, i.e. without cut-off on the detector. Other ratios are not precluded, however.

In some embodiments, the collimator comprises a fan beam collimator. A fan beam collimator comprises a collimator body having substantially continuous holes which according to the invention are directed at the two lines (astigmatism), wherein the second line is displaced towards infinity, whereby the radiation channels run in one direction (virtually) parallel. Preferably, the radiation lines run in this embodiment substantially parallel to a supporting surface of the supporting part, for example parallel to the table in which the introduction opening is found.

In one embodiment, the walls, or septa, between the holes are thin with respect to the hole cross section. Partly as a result, the sensitivity close to the collimator is still relatively constant, this in contrast to, for example, pinhole collimators which have close to the collimator precisely a kind of sawtooth sensitivity, with more or less blind spots in between the pinholes.

An embodiment of the scanner according to the invention having a fan beam collimator then offers an advantage that, especially in order to effectively scan the tissue close to the collimator, only few displacements of the collimator are necessary in order to still, however, scan the region fully. Were a pinhole collimator to be used, a very large number of steps would have to be taken, owing to the unfavourable relationship between the nett hole opening and the collimator surface area in the case of pinholes.

In some embodiments, the collimator comprises a slit-slat collimator. By a slit-slat collimator is here meant a stack of mutually spaced collimator plates (slats), with, placed in front of these, that is to say in between the slats and the receiving space, a collimator part having a plurality of gaps (slits). For example, only the collimator part with slits is then realized as a collimator part movable for the scanning, or the totality of slats and slits is realized as a collimator which is movable for the scanning. The combination of the slats and the slits defines the radiation channels. By, in the stack of plates, directing the plates individually and in total at the second line, for example, the radiation channels will also be directed at the second line. In some embodiments, the slit-slat collimator accordingly comprises a convergent stack of plates made of collimator material, as well as a plate-like collimator part having a plurality of substantially parallel slits. In one embodiment, the slits each have substantially parallel boundary wall surfaces or a knife edge. By substantially parallel boundary wall surfaces are here meant wall surfaces which are substantially flat and are all directed at the same line, in this case at the first line. The boundary wall surfaces then each lie on a plane which also contains the first line. All this is in contrast to, for example, a pinhole-like hole, the so-called knife edge, of which the boundary wall surfaces clearly diverge and thus define a triangular-pyramidal cross section. These latter are per se, however, likewise possible in the scanner, and comprise, in addition to the knife edge, also other edge shapes, such as a rounded edge.

In some embodiments, the detector extends, apart from the supporting part, at an angle to the longitudinal axis up to the longitudinal axis. This offers the advantage, for example, that the effect of the so-called dead part of many detector surfaces is moderated. The dead part is the (marginal) part which is not sensitive to the high-energy radiation. After all, if the detector stands obliquely to the receiving space, the relative contribution of the dead part is smaller. Even if the detector has no dead (marginal) part or not, this will still often be encircled by radiation screening material of a certain thickness. As a result, in one embodiment of the scanner, the detector must to some extent be placed downwards, which, in the case of an oblique placement, is relatively more favourable.

In some embodiments, the supporting part extends level with the detector above a plane extending through and parallel to the introduction opening. This implies that the supporting part, at a distance from the receiving space, is arched to above a plane spanned by the introduction opening to the receiving space, i.e. the introduction opening which is extended in all directions. This is, on the one hand, an anatomically attractive shape of the supporting part, wherein it is still, or even more than ever, easily possible to insert, or preferably drop the breast or some other body part deep into the receiving space. On the other hand, the shaping offers the advantage that the camera can be arranged such that any dead portion of the detector can be placed above the said plane through the introduction opening, so that less restrictions thus apply to the angles which can be scanned with the radiation channels of the collimator. These latter can now, for example, be placed yet more horizontally, or even allow a field of view of which the uppermost angles point somewhat upwards without that image part getting lost. Here "level with the detector" relates to that margin of the detector which is facing towards the supporting part. Note that now an oblique position of the detector is yet more advantageous, since, on the one hand, the dead part or the thickness of the screening is effectively compensated, whilst, on the one hand, a large part of the detector can be placed relatively close to the cavity, which is favourable for the sensitivity.

In embodiments the scanner comprises two cameras, in particular both of the same previously stated type with astigmatic collimator, on opposite sides of the receiving space. In a preferred embodiment, the scanner has precisely two cameras. The provision of a second camera in the scanner is more favourable for the total sensitivity, and thus a lower radiation load and/or shorter exposure time for the human to be examined is possible. The cameras are here preferably of the same type, and the arrangement is preferably symmetrical with respect to the receiving space, for example a vertical plane through the longitudinal axis of the receiving space, though that does not necessarily have to be the case.

In a possible embodiment comprising two cameras, the first lines thereof can coincide, for example coincident with the longitudinal axis of the receiving space, but that is not a requirement. It is also conceivable, for example, for each first line to lie closer to the collimator in question than the longitudinal axis.

In some embodiments, the collimator, for example the movable part of the collimator, comprises pinholes, which define the radiation channels, or at least a part thereof, for example in conjunction with a herein described stack of plates (slats). The pinholes offer the possible advantage of a wide field of view, though, for the scanning of nearby parts of the receiving space, with the breast or the like therein, more steps during the scanning movement of the movable collimator part are necessary than for some other configurations.

In a possible embodiment, a movable collimator part is provided with pinholes as radiation channels, and between that movable collimator part and the detector, at a distance from both and moving jointly with the movable collimator part, is placed a screening plate, made of material impermeable to the radiation and having openings therein which are aligned with the pinholes, such that projections of the pinholes onto the detector do not mutually overlap. For example, rectangular or square openings are provided in the screening plate. For example, the pinholes are directed at the said first line, for example with the first line in the receiving space, wherein the said second line lies in infinity. For example, the pinholes are realized as knife-edge pinholes.

In a second aspect, the invention provides a scanner, wherein the collimator defines and delimits a one-dimensional collection of radiation channels for the high-energy radiation, which radiation channels point towards a focal point located, with respect to the collimator, on the top side of and past the receiving space.

In this alternative embodiment, there is a column of radiation channels. For example, the column is placed in a movable collimator part in such a way that the column is directed parallel to the direction of movement of the movable collimator part. In another example, the column is directed parallel to the longitudinal axis of the receiving space. Through displacement of the collimator, or at least a movable collimator part thereof, the whole receiving space can preferably be scanned.

Alternatively, a single column of holes/radiation channels of a fan beam is also possible, which offers the advantage that the sensitivity close to the collimator surface is more even than in the case of pinholes.

In some embodiments, the collimator comprises a slit-slat collimator. That is in particular, once again, a convergent stack of plates made of collimator material, as well as a collimator plate having one slit, wherein the slit has, in particular, parallel boundary wall surfaces or an edge such as a knife edge.

Furthermore, a third aspect of the invention provides a scanner, in particular a scanner for scanning a human body part, such as a breast of a woman, with the aid of high-energy radiation, and comprising:

a supporting part for, during use of the scanner, supporting the upper body of the woman, and having therein an introduction opening with, below it, a receiving space for, during use, receiving the breast of the woman from above, at least one camera, placed under the supporting part during use, having a collimator and a detector which is arranged to convert high-energy radiation falling thereon into a signal, wherein a plane is spanned parallel to and through the introduction opening in the supporting part, wherein the receiving space extends downwards from that plane, wherein the supporting part has an elevated region on at least one side of the introduction opening, which elevated region lies above that said plane, wherein the detector is located at the bottom side of the supporting part and has an uppermost portion, possibly a dead surface part, which extends at least partially to above the plane.

The measure according to the above stated embodiment offers the advantage, already describe above, that the detector, which can often have a "dead" surface part, can place that dead part in an anyway already blind region, or in other words, that the radiation channels can be realized also roughly horizontally, or even pointing downwards to some extent, so that still somewhat more angle information can be obtained. The detector thus intersects the said plane through the opening. The type of camera or collimator which is used with this supporting part is not limited to the camera which is described for the scanner according to the first-named aspect of the invention, but rather is widely usable. The supporting part can be arched to above the said plane on one side of the opening, or the receiving space, though also on both sides. This latter offers the advantage that, if the camera is displaced, the same advantage can still of course be attained. Advantageously, however, two cameras are provided, on either side of the receiving space, or more than two, distributed around the receiving space.

In embodiments of this aspect of the invention, the supporting part is arched trapezoidally in cross section, that is to say the supporting part comprises by/around the introduction opening a flat plate part, contiguous thereto a rising part, advantageously on both sides of the receiving space or even round about, and, contiguous to the rising part, once again a flat part. The rising part can be linearly rising in cross section, or else rounded in cross section. The rising part can form, for example, a circumferential part around the flat part extending around the opening. The rising part can here be, for example, a part of a conical surface, or else have some other rising shape.

The receiving space itself can be cylindrical, wherein the camera(s) then have mutually parallel collimator surfaces and thus stand substantially parallel to each other. However, it is also possible to give the receiving space a conical cross section. In this case, a breast, for example, is compressed to some extent into conical shape during use of the device. The one or more cameras once again stand substantially parallel with the wall of the receiving space, and thus stand at an angle to the longitudinal axis of the receiving space.

The invention also relates to a scanner which comprises several aspects of the invention. For example, the scanner according to second and/or third aspect is provided with one or more details of the scanner according to the first aspect of the invention.

The invention also relates to a method for scanning a body part of a human, such as, for example, a breast of a woman, with the aid of high-energy radiation emitted by the body part, wherein use is made of a scanner as described herein.

The invention also relates to a breast scanner for scanning a breast of a woman, provided with a collimator as described herein.

The invention also relates to a breast scanner camera provided with a collimator as described herein.

The invention will now be explained with reference to the drawings, in which some non-limiting embodiments are shown.

DETAILED DESCRIPTION OF THE INVENTION

Figure 1:
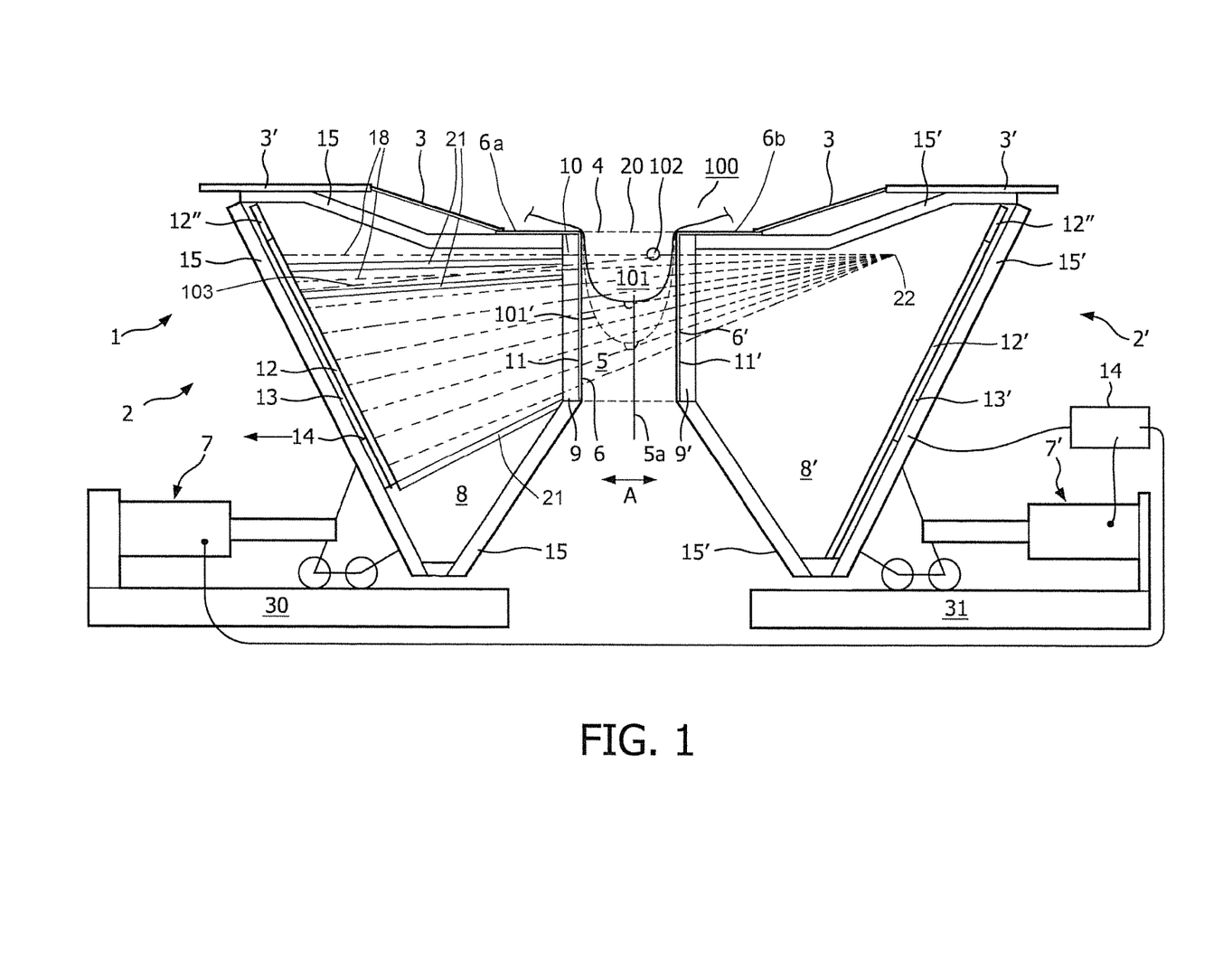
FIG. 1 shows schematically a scanner according to the invention, in side view in cross section.

FIG. 1 shows schematically an example of a scanner 1 according to the invention, in side view in cross section.

The shown scanner 1 has two cameras, denoted in general terms by 2 and 2', as well as a supporting part 3 for supporting the upper body 100 of a woman, and compression components 6, 6'.

In this example, the supporting part 3 is realized as a table, at least for laying of the upper body 100 thereon. In another embodiment, the table 3 is arranged to lay the whole person thereon. In yet another embodiment, the upper body 100 of the person is not horizontal but upright, for example in the case of a person whose breast or other body part is portrayed by the scanner 1 in a sitting or standing attitude. In these latter variants, the part 3 shall stand upright, or, for example, at an oblique angle.

The supporting part 3 has an introduction opening 4 having behind it, i.e., during use of the shown scanner 1, below it, a receiving space or cavity 5 for receiving a breast 101, 101' of a woman. The numerals 101, 101' here allude to breasts of different size.

In FIG. 1 is indicated a tumour 102 in the breast 101, 101', which tumour emits the high energy rays 103, for example gamma rays.

The scanner 1 is provided with two compression plates 6, 6' on either side of the space 5. The plates 6, 6' are permeable to the high-energy radiation 103. For example, the plates are made of plastic, for example of PMMA, polymethyl methacrylate. For example, the plates have a thickness between 3 and 8 millimeters.

By means of one or more compression actuators 7,7', the plates 6, 6' are movable towards each other and away from each other, in the directions of the double arrow A. The movement of the plates towards each other enables them to be pressed against the breast 101, 101', so that the breast is to some extent pressed flat.

The cameras 2, 2' each comprise an astigmatic collimator, which in this example is made up of a first collimator part 8, 8' and a second collimator part 9, 9. The collimator parts 8, 9 and 8',9' respectively together form a two-dimensional collection of radiation channels 10. The length of the channels 10 then forms a third dimension.

In the representation of FIG. 1, the radiation channels 10 of the camera 2 are indicated merely schematically for the sake of clarity, wherein the dashed line 18 indicates the principal direction of each channel 10. For example, or preferably, the camera 2' is designed with a collimator, possibly of two parts 8', 9', which defines and delimits an identical collection of radiation channels.

As will be explained below, at least the collimator part 9, 9' is a movable collimator part. The collimator part 9, 9' has on the side facing the space 5 an incident collimator surface 11, 11'.

The camera further comprises a detector 12, 12' and a reader 13, 13'. The readers 13, 13' are connected to a control unit 14, here additionally equipped as a signal processing device, of the scanner 1.

Each camera 2, 2' further has a housing 15, 15', which is impermeable to radiation and is constructed, for example, with plates of lead, wherein the detector 12, 12' and reader 13, 13', as well as the collimator parts 8, 8', are disposed in the chamber formed by the housing.

The scanner 1 here has a mirror-symmetrical structure having 2 cameras 2, 2' on either side of the space 5. The space 5 serves to receive, for example, a breast 101, 101' of a woman, of which only a part of the upper body 100 is shown here. The woman here lies on the, for example steel, supporting part or table 3.

It can be recognized that the compression plates 6, 6' have at their end, by the introduction opening 4, a flange 6a, 6a', which points outwards away from the space 5 and covers the housing of the camera 2, 2'. These flanges 6a, 6a' are in this example directed horizontally.

The space 5 is suitable for receiving, or can be suitably designed to receive a different body part, such as an arm, or else a larger breast 101'.

With the aid of the actuators 7,7', the compression plates 6, 6', and in this example the compression plates 6, 6' as a whole with the associated cameras 2, 2', can be moved towards each other in the direction of the double arrow A for the purpose of compressing the breast 101 and thereby being better able to scan.

In another embodiment there are one or more separate first adjusting actuators 7, 7' for adjusting the position of the compression plates 6, 6' and for thereby compressing the breast 101 in a desired measure, and one or more second adjusting actuators for positioning the cameras 2, 2' so that the collimator parts 9, 9' lie close to or against the plates 6, 6'. In addition, there are then one or more third actuators, or a collimator moving device 16, in order to realize a scanning movement which is yet to be described in greater detail.

In FIG. 1, it can be recognized that each camera 2, 2' rests on a straight guide 30, 31 in a frame (not further represented) of the scanner 1. The actuators 7 are then disposed between that frame and the camera 2, 2'.

The compression plates 6, 6' move jointly with the pressing movement of the actuators 7.

Each actuator 7,7' can be, for example, a pneumatic cylinder, or an electric spindle drive, and can be driven, for example, by the control unit 14 until a predetermined pressure is applied to the breast. The pneumatic actuator 7 can also be manually operated, such as with a small manually operated air pump, so that, for example, the woman or other patient can, herself/himself move the compression plates 6, 6' towards each other to a still acceptable pressure.

In the shown breast 101 is found a tumour 102, which is marked with radioactive markers and thereby emits gamma rays 103, of which only two are shown here. The gamma rays pass through radiation channels 10,10' of the collimators of the cameras 2, 2' and subsequently strike the detector 12, 12', which converts the radiation into a detectable signal, especially an electrical or light signal, which can be read by the reader 13, 13' and can be subsequently processed by the control and signal processing device 14. To this end, the device 14 comprises reconstruction software based on techniques which are known per se. Note that the control system can also comprise various control components, such as an actuator control and an image processing/reconstructor facility.

In FIG. 1, it is schematically indicated that the detector 12,12' can have a "dead" or "blind" part 12", which is not sensitive to the high-energy radiation, for example by virtue of a design or by a screen on the margin of the detector. This part 12" is here located under a raised region or part 3' of the support 3. That is to say, the part 3' lies higher than an imaginary plane 20 through the introduction opening 4 of the support. This proves not to be a problem for the woman who is lying thereon and still enables the breast 101 to be inserted deeply into the space 5. The placement of the detector 12 is now more favourable, however, since the collimator 8, 9 can make maximal use of the "seeing", sensitive part of the detector 12 and can inter alia, for example, measure angles, even horizontal to somewhat rising as in the figure.

The cameras 2, 2' will now be explained in greater detail with reference to FIGS. 2A, 2B, and 2C.

Figures 2A, 2B, 2C:
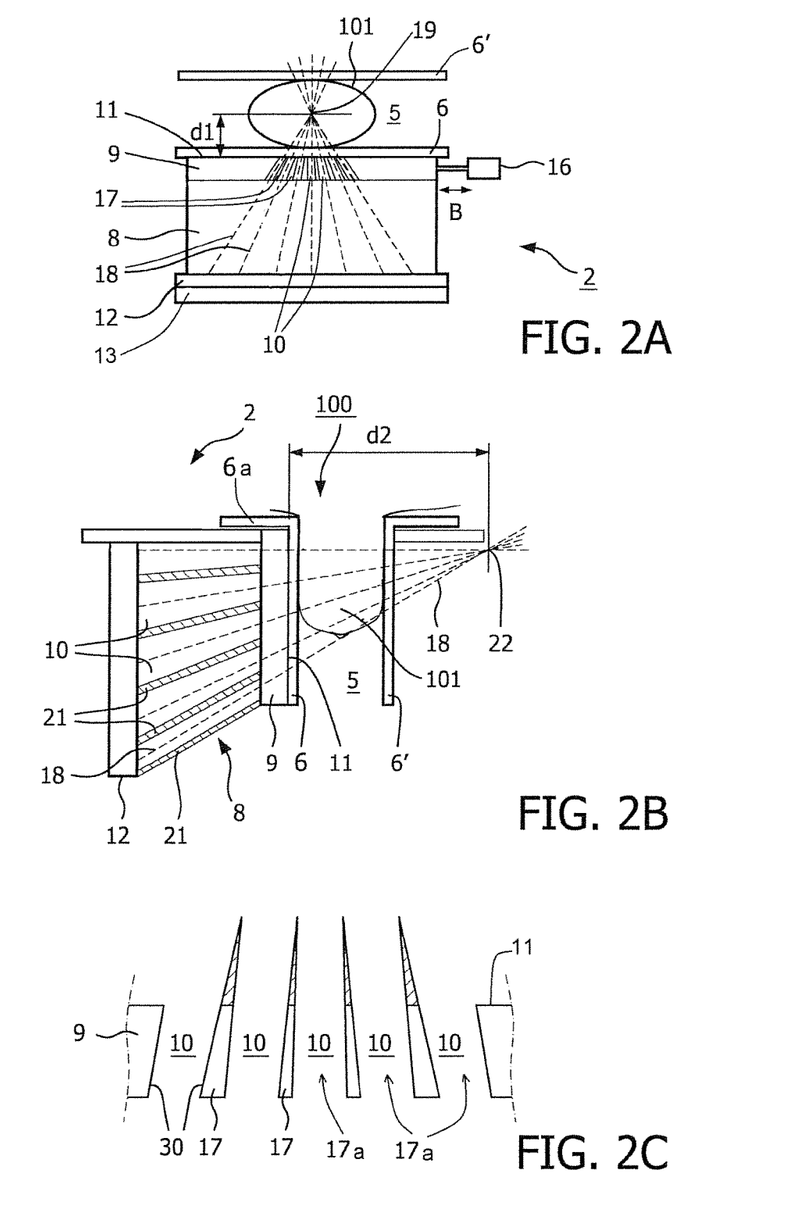
FIG. 2A shows a top view of a part of the scanner 1 of FIG. 1.
FIG. 2B shows a side view thereof.
FIG. 2C shows schematically a part of a possible slit component as the movable collimator part 9.

FIG. 2A shows a top view of a part of the scanner 1 of FIG. 1, and FIG. 2B shows a side view of a part of the scanner. FIG. 2C shows schematically a part of a possible slit component as the movable collimator part 9. In the figures, as in the rest of the drawing, similar components are denoted by the same reference numerals.

FIG. 2A shows a top view of a part of the scanner 1 of FIG. 1, with camera 2 (in part) and the breast 101. The collimator here comprises, once again, a first collimator part 8 and a second collimator part 9. The first collimator part 8 here comprises a stack of mutually spaced plates 21 ("slats") made of collimator material. In the representation of FIG. 1, a few of these plates or slats 21 are represented. The second collimator part 9 is a collimator plate having a series of gaps or slits 17a between limit wall surfaces or septa 17, and which form a part of the radiation channels 10, which are defined by the nett transmittance of the gaps in the second collimator part 9 and the spaces between the plates 21 of the first collimator part 8. For example, as here, the gaps 17*a* run parallel to the longitudinal axis 5*a* of the receiving space 5. The combination of gaps or slits 17*a* and behind-situated stacks of mutually spaced plates or slats 21 produces a two-dimensional collection of radiation channels 10.

Each radiation channel 10 has a principal direction of transmittance 18. This direction 18 is defined, for example, as the weighted average direction of transmittance for each channel. In the case of a symmetrical channel, that is, of course, the axis of symmetry. It is also possible to take the direction of greatest transmittance, whether averaged or not, over the smallest cross-sectional surface of the radiation channel. The principal directions of transmittance 18 of the radiation channels 10, viewed in projection onto the plane of the drawing, point towards a first line 19 represented in FIG. 2A.

In FIG. 2A, this first line 19 stands perpendicular to the plane of the drawing, and in the representation of FIG. 1 thus substantially vertically if the supporting part 3 is a horizontal table for the (upper) body, as is preferred. This first line 19 is chosen at a distance of d1 from the incident collimator surface 11. The distance d1 is, for example, a few centimeters, such as 2 to 5 cm. As a result, all radiation channels "look" towards one and the same part of the breast 101 close to the collimator surface 11 and the detector 12, thereby producing high sensitivity.

In the case of the symmetrical arrangement of cameras as in FIG. 1, it can also be sensible to make the first line 19 coincide with a longitudinal axis 5*a* of the space 5, in which case the compression plates 6, 6' are preferably simultaneously and symmetrically displaceable with respect to the, in FIG. 1, vertical longitudinal axis 5*a*. This arrangement leads to a still higher sensitivity in especially the region around the first line 19. In practice, this can only be achieved, however, by compressing each breast to be scanned to one and the same thickness, which, in the case, especially, of large breasts, can cause discomfort for the woman. In most cases, the respective first lines 19 of the cameras 2 and 2' will thus be situated at some distance apart, so that a larger part of the breast can be scanned, however, with relatively high sensitivity.

In addition, the camera 2 comprises a collimator moving device 16, which can displace at least, or preferably only, the second collimator part 9 in the direction of the double arrow B, in a practical embodiment, such as in the representation of FIG. 1, substantially horizontally, so that the situation of the first line 19 with respect to the breast 101 can thus be changed, and the part having the greatest sensitivity can be displaced from left to right, and thus the whole breast 101 can be scanned. Note that each detector 12, 12' is still of course sensitive next to the first line 19, yet merely less so.

If, of the camera 2, 2', only the second collimator part 9,9' needs to be moved by the thereto coupled collimator moving device 16, and the rest, such as in this case the collimator part 8,8', the detector 12, 12', the reader 13,13', and the housing 15,15', is kept stationary during the execution of a scan, as is preferred, the scan with the camera 2 can be conducted and completed faster than if the collimator with both parts 8 and 9 would have to be moved, or even also the whole collimator 8, 9 combined with the detector 12 (thus, in fact, the whole camera). Nonetheless, these are possible alternatives within the inventive concept.

FIG. 2B shows a side view of a part of the scanner 1 of FIG. 1. Here, the second compression plate 6' belonging to the second camera 2' is also shown.

The collimator if the first camera 2 comprises, once again, a first collimator part 8, of which the plates 21 made of collimator material can now be seen in cross section and between them, at least in conjunction with the second collimator part 9, define the radiation channels 10 with the principal direction of transmittance 18. These radiation channels 10 pass through a second line 22, which stands perpendicular to the plane of the drawing of FIGS. 1, 2B. The line 22 has a much greater distance d2 to the incident collimator surface 11 than the first line 19, which distance is denoted by d1. Although that has a negative influence on the sensitivity, it can clearly be seen that the whole breast 101 falls within the sensitivity of the camera 2, without the detector 12 acquiring an excessively large surface. To this end, the second line 22 lies at a distance d2 of, for example, 30 or 50 cm from the incident surface 11.

Note that both the distance d1 and the distance d2 are chosen in accordance with the (average) dimensions of the body part to be scanned. The stated dimensions are usable for breast scanners, but other dimensions are, of course, certainly possible.

The collimator shown in FIGS. 1 and 2A, B, C is a so-called slit-slat collimator, having, viewed from the space 5, a number of gaps or slits 17*a* in the movable part 9, followed by a number of plates or slats 21 in the collimator part 8, which slits 17*a* and slats 21 together define the radiation channels 10. The radiation channels 10 look towards a pair of lines 19, 22, which stand at right angles to each other and at a distance apart and thus form an astigmatic collimator.

Alternatives are certainly possible, such as an astigmatic fan beam collimator, in which the radiation channels are recessed in an, in principle, solid piece of collimator material. A fan beam collimator of this type can be produced, for example, by drilling of holes in a block of material, but is also conceivable with 3D print technologies.

Figure 3A:
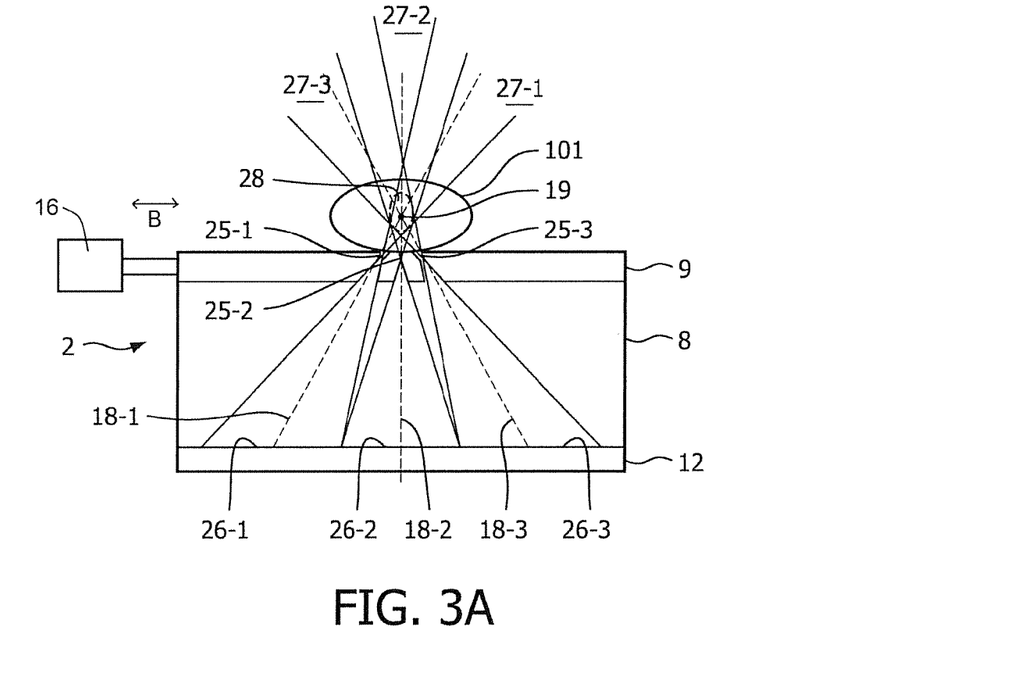
FIG. 3A shows in schematic cross-sectional view a camera 2 having an alternative collimator.
Figure 3B:
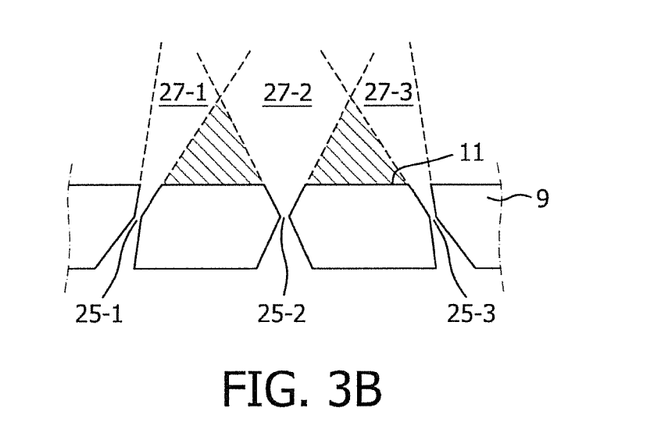
FIG. 3B shows a detail of the collimator part 9 of FIG. 3A.

With reference to FIGS. 3A and 3B, a camera 2 having an alternative collimator will now be explained. This collimator once again comprises a stack of plates (just as the plates 21) as the first collimator part 8, but now as the second collimator part 9 a plate part having therein a plurality of, for example three, pinholes 25-1, 25-2 and 25-3, which cast respective images 26-1, 26-2 and 26-3 of fields of view 27-1, 27-2 and 27-3 onto the detector 12, and herein define a focal volume 28 which is viewed through all the pinholes, or radiation channels. The pinholes 25 define with the plates 21 of the collimator part 8 once again radiation channels, having principal directions of transmittance 18-1, 18-2 and. 18-3, which meet in the first line 19.

The pinholes 25 are here disposed in a column directed parallel to the direction of movement B, which movement by the device 16 is realized during the scanning process.

In a variant, a plurality of columns of pinholes 25 are provided, each at different height viewed in the direction of the longitudinal axis 5*a*, so that a two-dimensional grid of pinholes 25 is present in the movable collimator part 9. For example, the radiation channels 10 are then jointly defined by a stack of plates 21 between the movable part 9 and the detector 12, or by a screening plate impermeable to radiation, having openings therein which are each aligned with a pinhole and are such that projections do not overlap one another on the detector 12.

The number of pinholes is here 3, but can also concern other numbers, such as 5, 10 et cetera. A difference between a second collimator part 9 of this type, having pinholes 25, and a second collimator having continuous holes is explained with reference to FIGS. 3B and 2C.

In FIG. 3B, the second collimator part 9 of FIG. 3A, having the three pinholes 25 with their respective fields of view 27, is shown. It can be seen that these fields of view close to the collimator surface 11 do not overlap and thus have reduced sensitivity, and that the shaded portions, even as a whole, are not seen. Passing along the collimator surface 11, the sensitivity of the camera 2 exhibits roughly a sawtooth. Consequently, the displacement of the collimator, at least of the movable part 9, must happen in a number of small steps in order to be able to effectively scan also breast tissue close to that collimator surface.

FIG. 2C shows schematically a part of a possible slit component as the second collimator part 9, 9', or, indeed, a detail of a possible fan beam collimator. Here the slits 17a which define a part of the radiation channels 10 are formed by septa 17 having substantially parallel limit wall surfaces 30. Since the septa 17 (either the material between the slits 17a, or the remaining material after drilling of the holes of the fan beam collimator) are relatively thin in comparison with the gaps 17a, the "blind part" (shaded) is much smaller than in a collimator with pinholes (see FIG. 3B), so that much smaller scanning movements need to be made.

Figure 4:
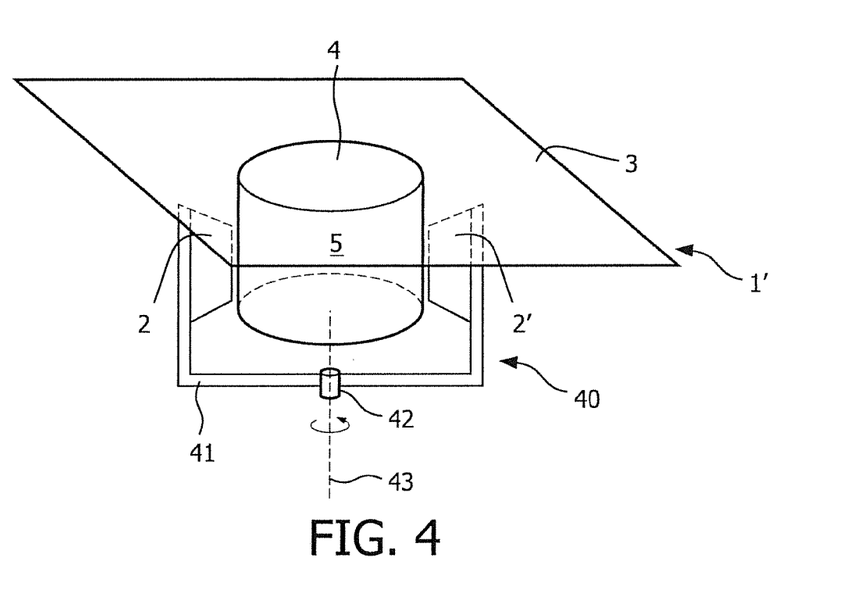
FIG. 4 represents schematically another scanner 1' according to the invention.

FIG. 4 represents schematically another scanner 1' according to the invention, having the two cameras 2, 2', a supporting part 3 having therein an opening 4 and, below it, a space or cavity 5, as well as a camera mounting 40, having a frame 41 and a rotator 42. A rotational axis is denoted by 43.

A body part, such as an arm or a breast, can be introduced into the space 5 via the introduction opening 4. After this, preferably no compression of the introduced body part takes place, but, if so desired, a compression device can be provided.

The cameras 2, 2' can scan the body part in the space 5 and, with the aid of the camera mounting 40, are rotated about the space 5. The cameras 2, 2' are suspended from or otherwise fastened to a rotating frame 41, which with a motor 42 or the like can be rotated about the axis 43. Thus the body part can be scanned at all angles.

Although it is in itself disadvantageous that the sensitivity will be lower for a non-compressed body part of this type, the comfort with this scanner is very high. The cameras 2, 2' are here preferably as described herein. That is not necessary, however, and in principle any type of camera which is sensitive to the high-energy radiation can even be used. This camera will, however, always comprise a collimator and a detector. Moreover, it is not necessary, but certainly advantageous, if the camera 2, 2' is mounted movably on the frame 41. An advantageous mobility is parallel to a tangent to the space 5 and parallel to the support 3. It can here be sufficient if only the collimator is moved, or only a part thereof, in accordance with that which is described in connection with FIG. 2A. Moreover, this collimator can be astigmatic, as according to other aspects of the present invention, but can also comprise focused pinholes, or a cone-beam collimator or a parallel-hole collimator, et cetera. It can here be favourable to choose the distance from the collimator surface to the site of greatest sensitivity at between one-quarter and three-quarters of the cross section of the space 5.

The invention claimed is:

1. A scanner for scanning a body part of a human with the aid of high-energy radiation emitted by the body part, the scanner comprising:
   a supporting part, which is arranged to, during use of the scanner, support the upper body of a human,
   a receiving space for the body part to be scanned, which receiving space has a longitudinal axis, wherein the supporting part is provided with an introduction opening via which the body part to be scanned can be introduced into the receiving space, the longitudinal axis extending through the introduction opening,
   at least one camera which is arranged to form an image of the body part introduced into the receiving space, with the aid of high-energy radiation emitted by the body part,
   wherein the camera comprises:
      a collimator, which comprises collimator material substantially impermeable to the high-energy radiation and which is disposed on a side of the receiving space, and
      a detector, which, viewed from the receiving space, is placed behind the collimator and which is sensitive to the high-energy radiation emitted by the body part,
   wherein the collimator comprises a movable collimator part, which has an incident surface facing towards the receiving space, wherein the camera comprises an associated collimator moving device which is arranged to move the movable collimator part in a direction of movement substantially parallel to the incident surface,
   wherein the collimator defines and delimits an astigmatic, two-dimensional collection of radiation channels for the high-energy radiation,
   which radiation channels point towards a first line, which extends at a first distance (d1) from the said incident surface and which is substantially parallel to the longitudinal axis of the receiving space,
   which radiation channels also point towards a second line, which extends on the opposite side of the receiving space relative to the collimator at a second distance (d2) from the said incident surface which is greater than said first distance (d1), which second line extends transversely to the first line and parallel to the said incident surface.

2. The scanner according to claim 1, wherein the direction of movement of the movable collimator part is substantially parallel to the second line.

3. The scanner according to claim 1, wherein the first line lies at a distance between 2 and 25 cm from the said incident surface.

4. The scanner according to claim 1, wherein the second line lies at a distance between 20 and 50 cm from the said incident surface.

5. The scanner according to claim 1, wherein the second line is located close to a plane through the introduction opening with a distance to that plane of no more than 5 cm measured in the direction of introduction and parallel to the longitudinal axis.

6. The scanner according to claim 1, wherein the collimator comprises one of a fan beam-collimator and a slit-slat collimator.

7. The scanner according to claim 1, wherein the collimator comprises a slit-slat collimator comprises a collimator plate having a plurality of substantially parallel slits and further comprises a convergent stack of mutually spaced plates made of collimator material, which stack is disposed between the collimator plate and the detector, wherein a collimator moving device is arranged to move the collimator plate back and forth in its plane.

8. The scanner according to claim 1, precisely containing two cameras on opposite sides of the receiving space.

9. The scanner according to claim 1, wherein the supporting part is a table, which is arranged to support the upper body of the human, which upper body lies on the table during use, and wherein the receiving space is located beneath the table, the longitudinal axis of the receiving space being substantially vertical.

10. The scanner according to claim 1 wherein the scanner comprises a compression device adapted to compress the body part received in the receiving space, wherein the compression device comprises a first and a second compression component, which are disposed on either side of the receiving space, wherein at least one of the said compression components is movable with respect to the other compression component in a compression direction, in order to compress the body part introduced into the receiving space.

11. The scanner according to claim 10, wherein the compression device comprises a compression component disposed between the movable collimator part and the receiving space, which compression component is permeable to the high-energy radiation emitted by the body part.

12. The scanner according to claim 10, wherein the compression device comprises a compression component disposed between the movable collimator part and the receiving space, which compression component is permeable to the high-energy radiation emitted by the body part, and wherein the compression component is mounted in the scanner so as to be movable together with the camera in said compressing direction, wherein a compression actuator is provided for moving the camera and the compression component.

13. A scanner for scanning a body part of a human with the aid of high-energy radiation emitted by the body part, the scanner comprising:
a supporting part, which is arranged to, during use of the scanner, support the upper body of a human,
a receiving space for the body part to be scanned, which receiving space has a longitudinal axis, wherein the supporting part is provided with an introduction opening via which the body part to be scanned can be introduced into the receiving space, the longitudinal axis extending through the introduction opening,
a first camera and a second camera disposed on opposite sides of the receiving space, wherein each of said first and second cameras is adapted to form an image of the body part introduced into the receiving space with the aid of high-energy radiation emitted by the body part,
wherein both the first and the second cameras comprise:
a collimator, which comprises collimator material substantially impermeable to the high-energy radiation and which is disposed on a side of the receiving space, and
a detector, which, viewed from the receiving space, is placed behind the collimator, and which is sensitive to the high-energy radiation emitted by the body part,
wherein the collimator comprises a movable collimator part, which has an incident surface facing towards the receiving space, wherein the camera comprises an associated collimator moving device which is adapted to move the movable collimator part in a direction of movement which is substantially parallel to the incident surface,
wherein the collimator defines and delimits an astigmatic, two-dimensional collection of radiation channels for the high-energy radiation,
which radiation channels point towards a first line, which extends at a first distance (d1) from the said incident surface and which is substantially parallel to the longitudinal axis of the receiving space, and
which radiation channels also point towards a second line, which extends on the opposite side of the receiving space relative to the collimator, at a second distance (d2) from the said incident surface which is greater than the said first distance (d1), which second line extends transversely to the first line and parallel to the said incident surface.

14. The scanner according to claim 13, wherein the supporting part is a table arranged to support the upper body of the human, which upper body part lies on the table during use, and wherein the receiving space is located beneath the table, wherein the longitudinal axis of the receiving space is substantially vertical.

15. A scanner for scanning a body part of a human with the aid of high-energy radiation emitted by the body part, the scanner comprising:
a supporting table, which is arranged to, during use of the scanner, support the upper body of a human,
a receiving space below said supporting table for the body part to be scanned, which receiving space has a vertical longitudinal axis, wherein the supporting table is provided with an introduction opening via which the body part to be scanned can be introduced into the receiving space, the longitudinal axis extending vertically through the introduction opening,
a compression device for compression of the body part introduced into the receiving space,
at least one camera, which is adapted to form an image of the body part introduced into the receiving space and compressed by the compression device, with the aid of high-energy radiation emitted by the body part,
wherein the camera comprises:
a collimator, which comprises collimator material substantially impermeable to the high-energy radiation and which is disposed on a side of the receiving space, and
a detector, which, viewed from the receiving space, is placed behind the collimator and which is sensitive to the high-energy radiation emitted by the body part,
wherein the collimator comprises a movable collimator part, which has an incident surface facing towards the receiving space, wherein the camera comprises an associated collimator moving device which is arranged to move the movable collimator part in a direction of movement substantially parallel to the incident surface,
wherein the collimator defines and delimits a two dimensional collection of radiation channels for the high-energy radiation,
which radiation channels point towards a first line, which extends at a first distance (d1) from said incident surface and which is substantially parallel to the longitudinal axis of the receiving space, and
which radiation channels pointed to said first line also extend substantially parallel to one another and to the supporting table.

16. A scanner for scanning a breast of a woman with the aid of high-energy radiation, the scanner comprising:
a supporting table for, during use of the scanner, supporting an upper body of a woman, said supporting table having therein an introduction opening for a breast of said women, wherein below said introduction opening a receiving space is present for, during use, receiving the breast of the woman introduced therein from above,
at least one camera, which is placed under the supporting table, and which has a collimator and a detector which is arranged to convert high-energy radiation that is emitted from the breast received in the receiving space, passes through the collimator, and then falls on the detector into a signal, wherein a plane is spanned parallel to and through the introduction opening in the supporting table, wherein the receiving space extends downwards from that plane, wherein the supporting table has an elevated region on at least one side of the introduction opening, which elevated region lies above that said plane, wherein the detector is located below the elevated region of the supporting table and has an uppermost portion which extends above that plane through the introduction opening.

* * * * *